(12) United States Patent
Roe et al.

(10) Patent No.: US 10,646,629 B2
(45) Date of Patent: May 12, 2020

(54) PLEURAL MANOMETRY CATHETER

(71) Applicant: Rocket Medical PLC, Washington (GB)

(72) Inventors: Edwin Richard Roe, Newcastle (GB); Richard Martin Varey, Pontefract (GB)

(73) Assignee: Rocket Medical PLC, Washington (GB)

( * ) Notice: Subject to any disclaimer, the term of this patent is extended or adjusted under 35 U.S.C. 154(b) by 117 days.

(21) Appl. No.: 15/028,691

(22) PCT Filed: Sep. 22, 2014

(86) PCT No.: PCT/GB2014/052871
§ 371 (c)(1),
(2) Date: Apr. 11, 2016

(87) PCT Pub. No.: WO2015/052488
PCT Pub. Date: Apr. 16, 2015

(65) Prior Publication Data
US 2016/0263296 A1 Sep. 15, 2016

(30) Foreign Application Priority Data

Oct. 11, 2013 (GB) .................................. 1318035.1
Mar. 28, 2014 (GB) .................................. 1405648.5

(51) Int. Cl.
*A61M 1/00* (2006.01)
*A61M 25/00* (2006.01)
(Continued)

(52) U.S. Cl.
CPC ............ *A61M 1/008* (2013.01); *A61B 5/036* (2013.01); *A61B 5/4836* (2013.01); *A61B 5/746* (2013.01);
(Continued)

(58) Field of Classification Search
CPC ....... A61B 5/036; A61B 5/4836; A61B 5/746; A61M 1/0025; A61M 1/008;
(Continued)

(56) References Cited

U.S. PATENT DOCUMENTS

| | | | | |
|---|---|---|---|---|
| 4,666,426 A | * | 5/1987 | Aigner | A61M 5/1582 604/6.16 |
| 4,777,951 A | * | 10/1988 | Cribier | A61M 25/0023 600/485 |

(Continued)

FOREIGN PATENT DOCUMENTS

| | | |
|---|---|---|
| CA | 1293169 A | 12/1991 |
| CN | 103055362 A | 4/2013 |

(Continued)

OTHER PUBLICATIONS

Brochure: Mirador Biomedical Compass Thoracentesis, Pleural Pressure Measurement Simplified, believed to have been published before Oct. 11, 2013, Catalog No. CTHR001.
(Continued)

*Primary Examiner* — Adam Marcetich
(74) *Attorney, Agent, or Firm* — Perkins IP Law Group LLC; Jefferson Perkins (57) ABSTRACT

A pleural manometry catheter comprises two tubes and a pressure transducer. The first tube provides a first flow path from the pleural cavity to the pressure transducer. The second tube provides a second flow path from the pleural cavity such that fluid can be drained from the pleural cavity. The pressure transducer comprises a processor for processing, continuously, the real-time fluctuations in the pressure of the second flow path and therefore the pleural cavity as fluid is aspirated from it via the first tube.

12 Claims, 5 Drawing Sheets

(51) Int. Cl.
*A61M 39/22* (2006.01)
*A61B 5/03* (2006.01)
*A61B 5/00* (2006.01)

(52) U.S. Cl.
CPC .......... *A61M 1/0025* (2014.02); *A61M 25/00* (2013.01); *A61M 25/003* (2013.01); *A61M 39/22* (2013.01); *A61M 2025/0003* (2013.01); *A61M 2025/0031* (2013.01); *A61M 2025/0037* (2013.01); *A61M 2025/0039* (2013.01); *A61M 2205/18* (2013.01); *A61M 2205/3344* (2013.01); *A61M 2210/101* (2013.01)

(58) Field of Classification Search
CPC .. A61M 2025/0003; A61M 2025/0031; A61M 2025/0037; A61M 2025/0039; A61M 2205/18; A61M 2205/3344; A61M 2210/101; A61M 25/00; A61M 25/003; A61M 39/22; A61M 1/0027; A61M 2025/0004; A61M 2205/3331
See application file for complete search history.

(56) References Cited

U.S. PATENT DOCUMENTS

| | | | | |
|---|---|---|---|---|
| 5,106,363 | A * | 4/1992 | Nobuyoshi | A61M 25/104 604/523 |
| 5,108,364 | A * | 4/1992 | Takezawa | A61M 1/0084 600/549 |
| 5,207,648 | A * | 5/1993 | Gross | A61M 25/0014 604/164.09 |
| 5,527,280 | A * | 6/1996 | Goelz | A61J 15/0015 604/103.1 |
| 6,251,079 | B1 * | 6/2001 | Gambale | A61M 25/0068 600/486 |
| 6,295,990 | B1 * | 10/2001 | Lewis | A61B 17/22 128/898 |
| 2004/0049157 | A1 * | 3/2004 | Plishka | A61B 17/3415 604/164.09 |
| 2005/0038413 | A1 * | 2/2005 | Sansoucy | A61M 25/003 604/537 |
| 2005/0080398 | A1 * | 4/2005 | Markel | A61M 25/0014 604/508 |
| 2005/0203469 | A1 * | 9/2005 | Bobroff | A61M 1/0003 604/318 |
| 2007/0078444 | A1 * | 4/2007 | Larsson | A61M 1/0031 604/540 |
| 2007/0083157 | A1 * | 4/2007 | Belley | A61M 25/0606 604/93.01 |
| 2007/0112302 | A1 * | 5/2007 | Yu | A61M 25/0606 604/164.01 |
| 2008/0091104 | A1 * | 4/2008 | Abraham | A61B 8/0841 600/439 |
| 2008/0167607 | A1 * | 7/2008 | Pfeiffer | A61B 5/036 604/97.01 |
| 2011/0119224 | A1 * | 5/2011 | Mangione-Smith | A61B 6/12 706/52 |
| 2011/0154241 | A1 * | 6/2011 | Skidmore | A61M 16/0051 715/771 |
| 2012/0029354 | A1 * | 2/2012 | Mark | A61B 17/32002 600/439 |
| 2012/0075122 | A1 * | 3/2012 | Whitlow | A61B 5/18 340/963 |
| 2013/0110057 | A1 * | 5/2013 | Croteau | A61M 1/0031 604/318 |
| 2014/0088567 | A1 * | 3/2014 | Nieman | A61M 1/0084 604/533 |
| 2014/0343462 | A1 * | 11/2014 | Burnet | A61B 5/1101 600/595 |

FOREIGN PATENT DOCUMENTS

| | | |
|---|---|---|
| WO | 9421315 A1 | 9/1994 |
| WO | 2012162848 A1 | 12/2012 |
| WO | 2013003970 A1 | 1/2013 |

OTHER PUBLICATIONS

Peter Doelken, John T. Huggins, Nicholas J. Pastis and Steven A. Sahn, Pleural Manometry: Technique and Clinical Implications, journal (Chest), Dec. 2004, pp. 1764-1769, vol. 126, American College of Chest Physicians.
Brochure: Mirador Biomedical Compass Thoracentesis, Pleural Pressure Measurement Simplified, Catalog No. CTHR001.
Peter Doelken, John T. Huggins, Nicholas J. Pastis and Steven A. Sahn, Pleural Manometry: Technique and Clinical Implications, Chest 2004; 126; 1764-1769, American College of Chest Physicians.
International Search Report and Written Opinion of the International Searching Authority, PCT/GB2014/052871, May 12, 2014.

* cited by examiner

PLEURAL MANOMETRY CATHETER

FIELD OF THE INVENTION

The invention is in the field of a pleural manometry catheter. In particular, the catheter is for use in human patients and for treatment of pleural effusions for diagnostic and therapeutic purposes. The invention is also an apparatus and a device for conducting pleural manometry comprising a pleural manometry catheter. In particular, the device is a pleural manometry catheter for measuring changes in chest cavity pressure in real time.

BACKGROUND AND PRIOR ART

Thoracentesis is an invasive procedure to remove fluid or air from the pleural space for either diagnostic or therapeutic purposes; a cannula, hollow needle or catheter, is introduced into the chest and pleural fluid is aspirated through it.

With regard to the diagnostic purposes, pleural fluid can provide information enhancing the practitioner's understanding of the underlying pleural pathophysiology when an effusion is present, thereby allowing the source and/or cause of the pleural effusion to be found—common causes include cancer, congestive heart failure, pneumonia and tuberculosis, as well as recent surgery.

With regard to the therapeutic purposes, thoracentesis can be useful when a large volume of fluid is present; such removal will tend to improve patient comfort and lung function. Second, the measurement of pleural pressure also helps to differentiate between lung entrapment and trapped lung, and as such allows for the safer removal of large effusions. Third, it is a useful tool to select appropriate patients with malignant pleural effusions for pleurodesis.

Pleural manometry during large-volume procedures allows the practitioner to monitor changes of pressure during those procedures and thus to avoid pleural pressures (i.e. below below $-20$ cm H2O) which are excessively negative—pressures which might otherwise lead to the onset of re-expansion pulmonary edema. In addition, measurement of lung elastance by way of pressure has been proven to be a predictor of successful pleurodesis.

In *Pleural manometry: Technique and Clinical Implications*, Doelken et al (Chest 2004; 126; 1764-1769), two widely used means of pleural manometry—namely a vertical-column water manometer with an interposed resistive element, and a haemodynamic transducer connected to a standard physiologic system—are discussed, along with the disadvantages of both. The paper goes on to present a system of pleural manometry comprising a flexible thoracentesis catheter and a water manometer consisting of two lengths of IV tubing connected through a 22 gauge needle inserted into an injection terminal. This system is connected to the zeroing port of a pressure transducer and, once both are purged of air, and the electronic system is zeroed at the level the thoracentesis catheter is introduced into the patient, measurements can be performed initially and after each 250 ml of fluid is withdrawn.

Disadvantageously, this is not a real-time system and as such the dynamic measuring of lung pressure cannot be undertaken. In any context, but particularly in an emergency context, where lung pressure is likely to change swiftly, such start-stop measurement is sub-optimal, as well as being an unwieldy and therefore impracticable procedure.

The closest known prior art consists of the "Compass" thoracentesis device by Mirador medical. The Mirador device requires the movement of the fluid through the manometer, along a tube, and through a first one-way valve to a reservoir such as a syringe barrel. The user must then pause after aspiration of a first quantity of fluid to take a measurement from the manometer, before ejecting the fluid through a second one way valve. After this, aspiration can be done in real time.

Because the fluid must travel through the manometer, the Compass manometer itself will be thrown away after a single use.

Further, prior to the aspiration of the first quantity of fluid, the manometer cannot be used to measure the pleural fluid pressure. Instead, during this period, a large negative pressure is observed; this is not the patient's pleural pressure, this is the pressure being generated by the drainage system.

Further, the assembly of apparatus comprises several parts which must be assembled before the procedure takes place, and this can be unwieldy.

The prior art devices share the disadvantage that they all take rather a long time to use—in particular, they all require a calibration step to be undertaken, which is time consuming and requires a certain amount of prior knowledge in order to be effected. It is possible to envisage a situation in which the user does not know how to prime a prior art manometer and as such produces data which is inaccurate, leading to mistreatment of the patient.

Current practice has been that after insertion of the catheter in to the pleural space the operator would have to prime the catheter and allow fluid to be placed over the transducer. The manometer of the invention allows for measurement directly after insertion.

It is amongst the aims of the invention to attempt solutions to these and other problems.

SUMMARY OF THE INVENTION

In a first broad, independent aspect, the invention comprises a pleural manometry catheter, the catheter comprising a first tube, a second tube and a pressure transducer, wherein the first tube comprises a first end and a second end, wherein the first end is, in use, disposed inside the pleural cavity and wherein the second end, in use, projects from the pleural cavity and comprises a first flow path to the pressure transducer, wherein the first end of the first tube comprises at least one aperture and in use, pleural fluid flows through the aperture along the first flow path to a pressure transducer, wherein the second tube comprises a first end and second end, wherein the first end is, in use, disposed inside the pleural cavity and wherein the second end projects from the pleural cavity to the s exterior and wherein the inner tube further comprises at least one aperture at or near the first end of the tube comprising a second flow path such that fluid may flow through the said aperture and along the tube from the first end to the second end, such that the fluid can be drained from the pleural cavity and wherein the pressure transducer is configured so as to detect real-time changes in the fluid pressure of the first flow path, such that icy when in use, fluid is drained from the pleural cavity along the second tube, the sensor in communication with the first tube detects a concomitant drop in fluid pressure in the fluid in the first tube.

This configuration provides an effective means of real-time monitoring Such monitoring of pleural pressure allows for the safe drainage of large volumes of pleural fluid as it permits the practitioner to continuously check that the drainage is occurring within safe parameters i.e. that the procedure is terminated if the pleural pressure drops below $-20$ cm $H_2O$. Real time pressure monitoring enables the user to determine if there is a large (negative) change in pressure during pleural fluid removal, which may be symptomatic of trapped lung: quick diagnosis of this is essential for ongoing patient care and real-time monitoring allows for such a diagnosis. Real time pressure monitoring is naturally advantageous in environments where quick but non-life threatening chest drainage is of importance, such as in emergency rooms. The real time measurement is very clearly advantageous over the prior art process discussed in the foregoing paragraphs of draining a given amount, stopping the drainage and then measuring chest pressure.

A further advantage of the system is that, in providing data crucial in provoking actions to maintain pleural pressure above −20 cm H2O, the manometer contributes to the reduction of the risk of the occurrence of re-expansion pulmonary edema, which otherwise currently develops in about 1% of thoracentesis procedures.

In this configuration, the pressure monitoring function and the draining function of the catheter work in parallel rather than in series as in the prior art, thus providing a speedier path to first measurement and allowing for swifter simultaneous drainage and pressure monitoring the prior art requires the movement of fluid in and out of a syringe or the like, in order to aspirate fully. With the apparatus discussed herein, the drainage and measurement may be undertaken in a continuous motion.

A further, unexpected and very marked advantage of the device of the invention is that there is no need for a priming step in order to use the manometer of the invention, the operator can zero the unit before catheter insertion, insert the catheter and then measure the pressure in the pleural space immediately without having to go through a separate priming procedure.

This primary advantage has a number of advantageous effects. First and foremost, pleural manometry catheter can start to be used more quickly without the priming step. Starting more quickly may lead to the reduction of the duration of the operation overall is Second there is no need to undertake, or even know how to undertake, a separate priming procedure. As such, a wider cross-section of users may operate the device, and this can be particularly important in an emergency context, wherein the catheter must be inserted and used quickly and in other instances staff knowledgeable of the priming step may not be available.

Third, removal of the calibration step leads to lighter, more portable and smaller apparatus—a more usable pleural manometry catheter.

Preferably, the second, inner tube is of a lesser diameter than the first, outer tube and runs along the internal bore of the outer tube, such that there is a space between the outer diameter of the inner tube and the inner diameter of the outer tube, and wherein at least a part of the flow path between the aperture of the first tube and the pressure transducer comprises the space between the said inner and outer tubes.

A double skinned catheter of the sort described above has the advantage of providing a single projection into the plural cavity, thereby minimising the size of the aperture required for chest drainage and further minimising the amount of potential damage caused by the insertion of the catheter.

Preferably the catheter further comprises a valve attached to the second end of the second tube and being in fluid communication with the second tube, and wherein the valve is biased shut.

More preferably, the valve can only be opened by the projection of a solid object, such as a syringe needle, in the opposite direction to the, in use, flow path through the second tube.

The provision of a valve of this type provides a simple means of sealing the catheter when not in use and automatically opening it when in use—i.e.when a syringe is inserted into the proximal end into the second tube ready for aspiration.

Preferably, the first tube comprises a flow path comprising two portions, wherein the first portion comprises the first tube and wherein the second portion is substantially perpendicularly disposed to the first portion.

The provision of tubes perpendicularly disposed to one another provides a clear separation for the user of the function of the two tubes, thereby enabling the user to distinguish between the two tubes in a hurried or emergency situation.

Preferably, the internal bore of the first end of the first tube comprises a tapered portion and wherein the said internal bore tapers so as to form a touching fit with the inner tube.

Providing a tapered portion of this sort allows for the introduction of the two tubes—one inside the other into the subject/patient's pleural aperture with the minimum of added disruption over and above what would be caused by a single tube—there is no "step" or second barrel to cause additional injury.

Preferably, the inner tube comprises a first, substantially straight portion and a second, curved portion.

Provision of the curved portion (not shown) of the catheter decreases the chances that the catheter will damaging items in the pleural cavity; it no longer presents a pointed portion to the interior of the chest.

Preferably, the second portion is resiliently deformable.

By making the portion resilient lead deformable, damage to items in the pleural cavity is further militated against.

Preferably, the apertures of the inner tube are disposed along the inner diameter of its second, curved portion.

Arranging the apertures in this way i.e. by providing multiple apertures but also by locating them on the internal curve of the distal end of the catheter, inside the curve, the apertures are protected against blockage.

Preferably, the apertures of the inner tube are oval in shape.

Preferably, the catheter further comprises a plate, and wherein said plate is fixed relative to the catheter, said plate being disposed such that it dictates which proportion of the length of the catheter can be inserted into the chest of the patient.

The plate provides that the catheter is only inserted to a particular chest depth. A further advantage of the plate is a degree of stability to the apparatus which aids measurement. A third advantage is that the plate provides a point of purchase on the chest of the patient.

More preferably, the surface of the plate occupies a plane substantially perpendicular to the direction of the first portion of the second tube.

A perpendicular plate allows for a flush fit onto the patient's chest, which stabilises the the catheter against disruption.

Preferably, the catheter further comprises a stabiliser for keeping the catheter firmly retained in place.

The addition of the stabiliser allows for quicker and more accurate measuring of pleural pressure.

Preferably, the pressure transducer comprises an alarm to alert the user to a fall in pleural cavity pressure proximate to a given level.

More preferably, the alarm intensifies the nearer the pleural pressure reaches the given level.

The use of an alarm is particularly useful in an emergency setting wherein it may not be possible—what with the need to do other tasks at the same time—to continuously monitor any display provided by the monometry system. The alarm provides the means of bringing the practitioners attention to the issue of extreme negative pressure if and only if that issue arises. Provision of the alarm and moreover an alarm which intensifies the nearer to the set terminal level the negative pressure sinks, provides a useful means of drawing the practitioners attention to the device when that attention is needed.

The invention also comprises a pleural manometry catheter substantially as described herein, with reference to any appropriate combination of the text and/or drawings.

In a second broad, independent aspect, the invention comprises a method of draining the chest of a patient, the method comprising the following steps, in this order: inserting both the first and second tubes into the pleural cavity such that the first end of each tube projects into the pleural cavity and the second end of each tube projects into the exterior. Draining fluid from the pleural cavity through the second tube, and using a pressure transducer to measure real time changes in the fluid pressure of the first flow path, such that when in use, fluid is drained from the pleural cavity along the second tube, the sensor in communication with the first tube detects a concomitant drop in fluid pressure in the fluid in the first tube.

The invention also comprises a method of draining the chest of a patient, substantially as described herein, with reference to any appropriate combination of the text and/or drawings.

In a third broad, independent aspect, the invention comprises a method of draining a liquid, the method comprising the following steps, in this order; inserting both the first and second tubes into the pleural cavity such that the first end of each tube projects into the pleural cavity and the second end of each tube projects into the exterior, draining fluid from the pleural cavity through the second tube, and using a pressure transducer to measure real time changes in the fluid pressure of the first flow path, such that when in use, fluid is drained from the pleural cavity along the second tube, a sensor in communication with the first tube in the detects a concomitant drop in fluid pressure in the fluid in the first tube.

The invention also comprises a method of draining a liquid, substantially as described herein, with reference to any appropriate combination of the text and/or drawings.

The foregoing methods comprise a particularly effective means of monitoring the chest drainage of a patient in real time and more generally a means of draining a liquid in real time.

BRIEF DESCRIPTION OF THE FIGURES

The invention will now be described with reference to the figures, of which.

DETAILED DESCRIPTION OF THE PREFERRED EMBODIMENTS

Figure 1:
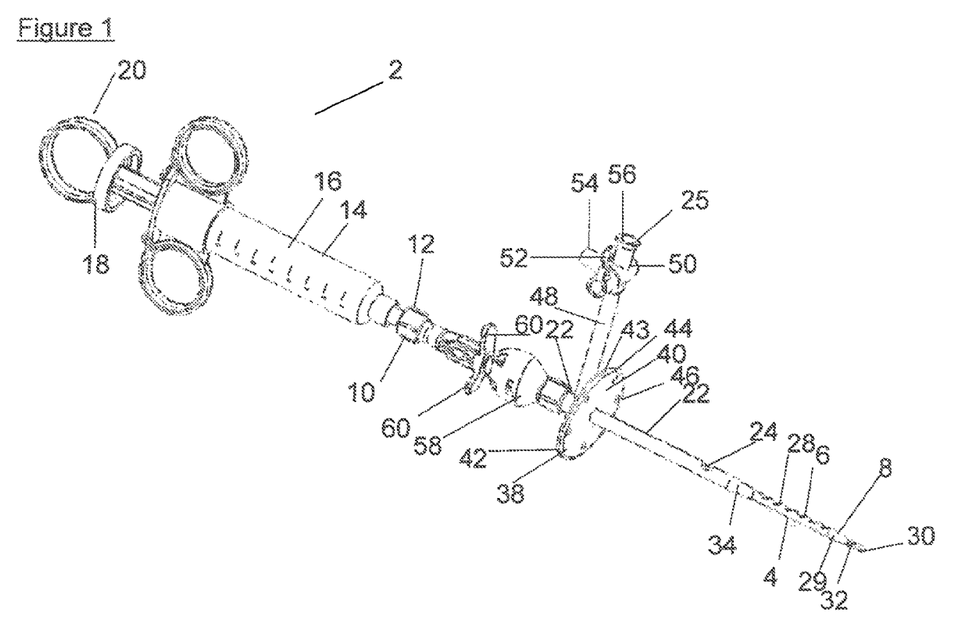
FIG. 1 is a diagrammatic perspective side view of a catheter of the invention, attached to a syringe.
Figure 2:
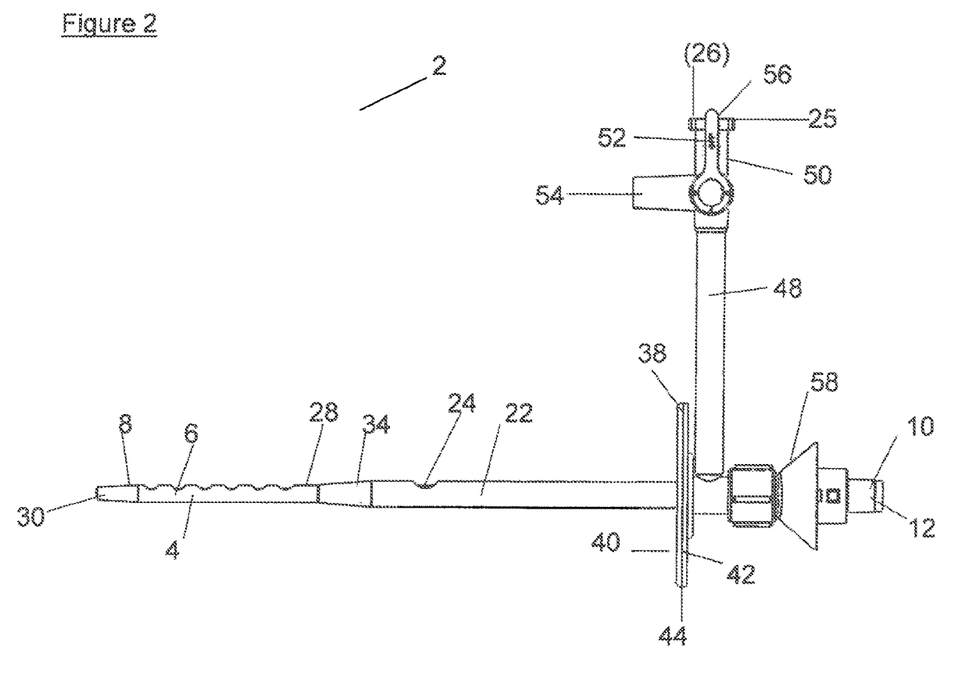
FIG. 2 is a diagrammatic side view of a catheter of the invention.

At FIG. 1, there is shown a pleural manometry catheter, indicated generally at 2. The catheter 2 comprises a first tube 4 comprising a first flow path running from the apertures 6 located at the distal end 8 of the catheter 2, to attachment 10, which in preferred embodiments is a luer connector, at the proximal end 12 of the catheter 2; the attachment 10 allows connection of the catheter 2 to a syringe 14 or other drainage device or system. The catheter 2 may, in some preferred embodiments, comprise an integrated drainage device such as an integrated syringe. Here the syringe 14 is not integrated, being of conventional construction and comprising a barrel 16 and a plunger 18 attached to a handle 20, the syringe being so arranged that when the plunger 18 is pulled via the handle 20, negative pressure is asserted such that fluid may be pulled along the first tube 4 into the barrel 16 of the syringe 14. The catheter 2 is presented to the practitioner as a single integrated unit, it is not necessary to attach additional tubing to the catheter 2 in order to make it work.

The catheter 2 further comprises a second tube 22, comprising a second flow path running from the aperture 24 located adjacent the distal end 8 of the catheter 2, to terminus 25, where a pressure transducer 26 (not shown), such as a digital manometer may be fitted. The catheter 2 is shown without a pressure transducer 26 attached as it is possible to supply the catheter 2 without the said pressure transducer 26, allowing a practitioner-preferred transducer to be fitted, in other preferred embodiments, a pressure transducer 26 such as a digital manometer is supplied as an integrated part of the catheter 2 or as an attachment.

In use, the tubes 4, 22 are inserted into the pleural cavity via an aperture in the patient's chest. The pleural fluid is aspirated through first tube 4 into the shown syringe 14 or another receptacle. Pressure changes in the liquid present in the second tube 24 are monitored by the pressure transducer 26, which provides real-time feedback. The second flow path is entirely separate from the first flow path; fluid does not flow through the transducer 26 in order to be aspirated.

In preferred embodiments, the distal end 8 of the catheter 2 is "double skinned", which is to say that one tube lies within the other. In this embodiment, the aspiration line—the first tube 4—has a lesser diameter and runs along the internal bore of the manometer line—the second tube 22. This arrangement could be reversed, or the tubes could be separate, with neither tube inside the other; a further preferred embodiment would comprise two tubes connected along their length—connected side by side, or one atop the other; the skilled man will be able to experiment with other configurations of double and multi-lumen catheter.

First tube 4 comprises a plurality of apertures 6, disposed along the, in use upper side 28 of the distal end 8 of the catheter. The apertures, which preferably number three or more, and less than ten, are preferably oval in shape and are preferably arranged in a single row. The distal end 8 tapers along first tapered portion 30 to a tip 30 which in preferred embodiments is solid and does not feature an aperture at its end. However, in the shown embodiment, there is a further aperture 32 disposed immediately prior to the tip 30.

The dual nature of the preferred embodiments of the catheter 2 discussed above has the effect of allowing immediate insertion of the catheter 2 into the patient in use, without priming, since pressure can be accurately measured via the manometer line or second tube 22, whilst aspiration independently occurs through the first tube 4 or aspiration line.

The first tube 4 joins the second tube 22 at second tapered portion 34, which provides a smooth gradation between the respective diameters of the tubes, in some preferred embodiments, not shown, the first tube 4 is curved, in use, upwards, such that the upper side 28 is curled in on itself, with the apertures 6 therefore running along the internal path of the curve. The second tube may have a sealed end 36 (not shown) or it may alternatively be terminated by tapered portion 34, which may form a watertight seal, a touch fit and a frictional fit with first tube 4 in different embodiments. The first tube 4 runs in some embodiments along the centre of the inside of the second tube 22, but in other preferred embodiments may rest on or be joined at one or more points to the internal wall of said second tube.

At least the first tube 4 and preferably both first and second tubes 4, 22 are made of resiliently deformable plastics materials. Generally, the catheter 2 is made of one of more of the following groups of materials; metals, alloys, plastics, glass.

The tubes 4, 22 run through plate 38, which comprises planar sides 40, 42, and a rounded off or bevelled edge portion 44, as well as a plurality of apertures 46. in the current embodiment, the plate 38 lies on a plane perpendicular to that of the tubes 4, 22. The apertures 46 can be combined with an attachment, such as one or more elongate belts or strips of hook and loop portion, to secure the catheter 2 to the patient.

Beyond the plate 38, the formally parallel or substantially parallel paths of the two tubes 4, 22 cease to be parallel, as the second tube branches off, with the offshoot tube 48 being disposed substantially perpendicularly to the second tube 22. The offshoot tube comprises a valve 50 which comprises a handle 52 and is switchable between terminus 25 and second terminus 54, Terminus 25 preferably comprises a luer connection 56 and may be attached to a manometer. Second terminus 54 may be attached to a means of aspiration.

Figure 3:
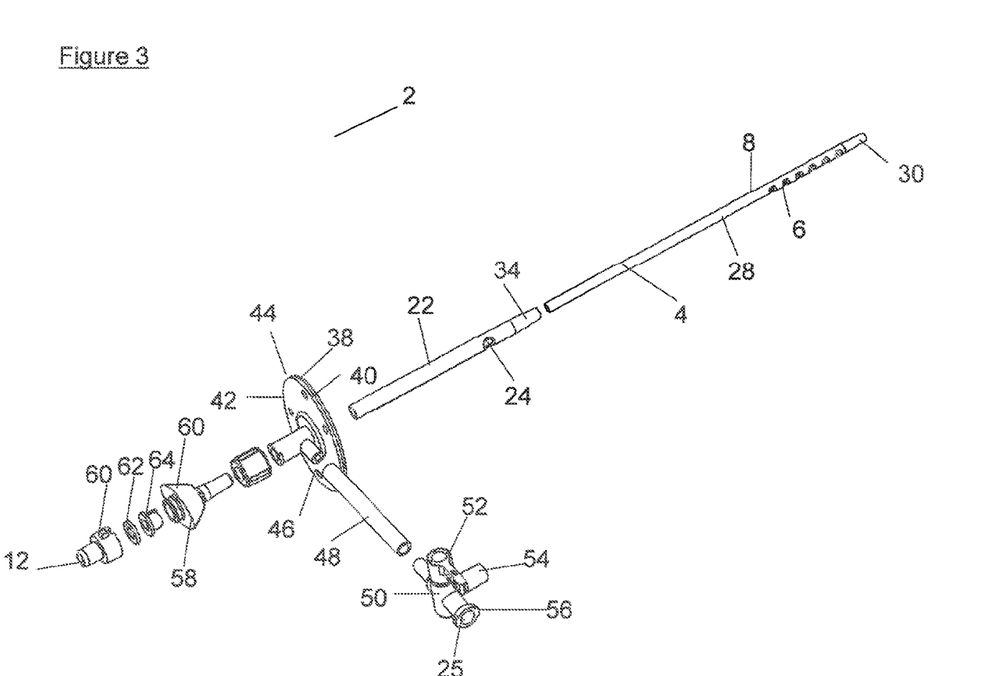
FIG. 3 is an exploded diagrammatic perspective side view of a catheter of the invention.
Figure 4:
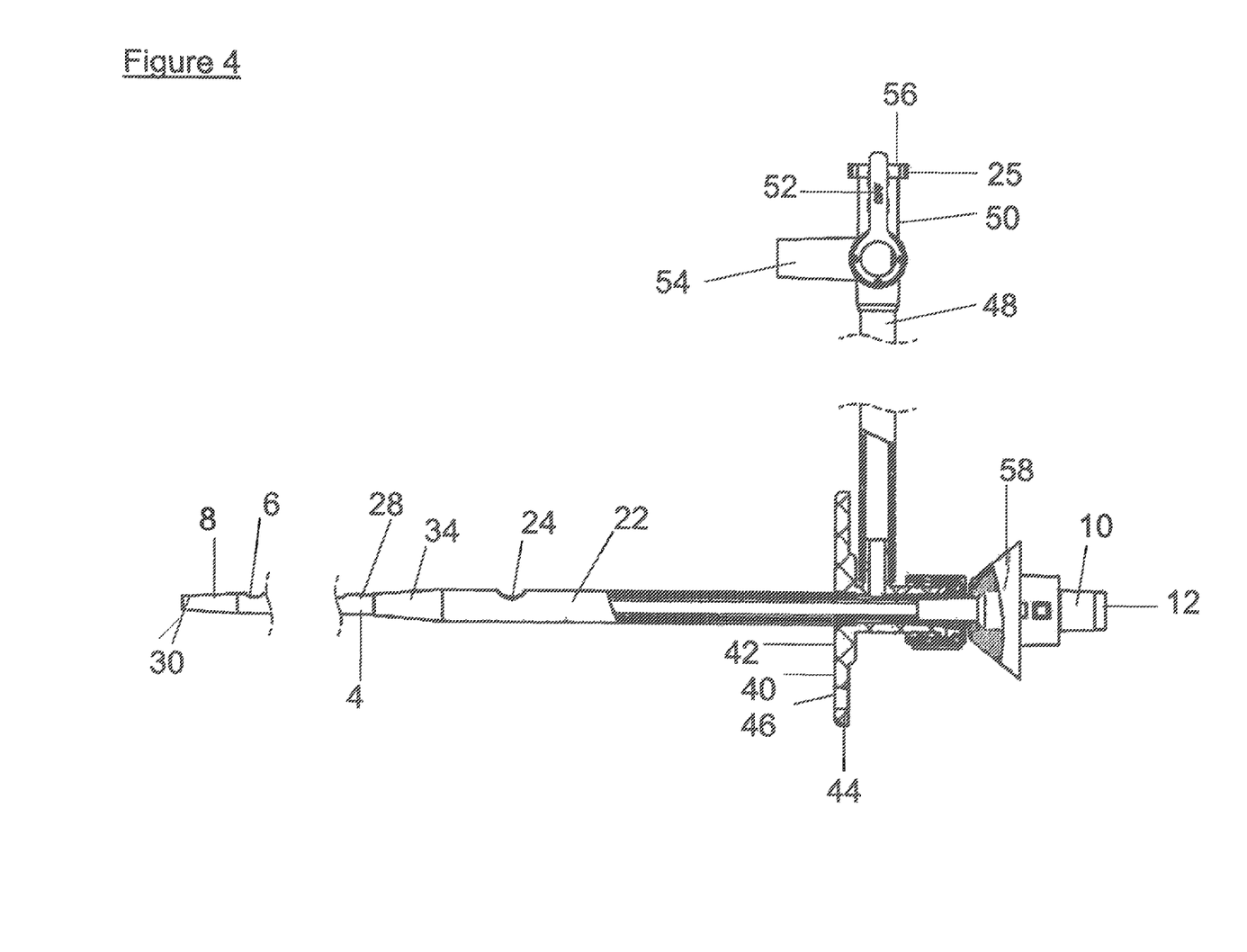
FIG. 4 is a diagrammatic side view of the invention rendered in partial cross-section.

First tube 4 joins valve 58. Valve 58 is opened only by the pushing of the end of syringe 14 or another elongate tool through the said valve 58. Valve 58 comprises a pair of projections 60 which can be grasped by the practitioner during the connection of the syringe 14 to the catheter assembly. At FIG. 3, it can be seen that the valve 58 comprises a pair of housing portions 60, a base 62 and a top 64.

Figure 5:
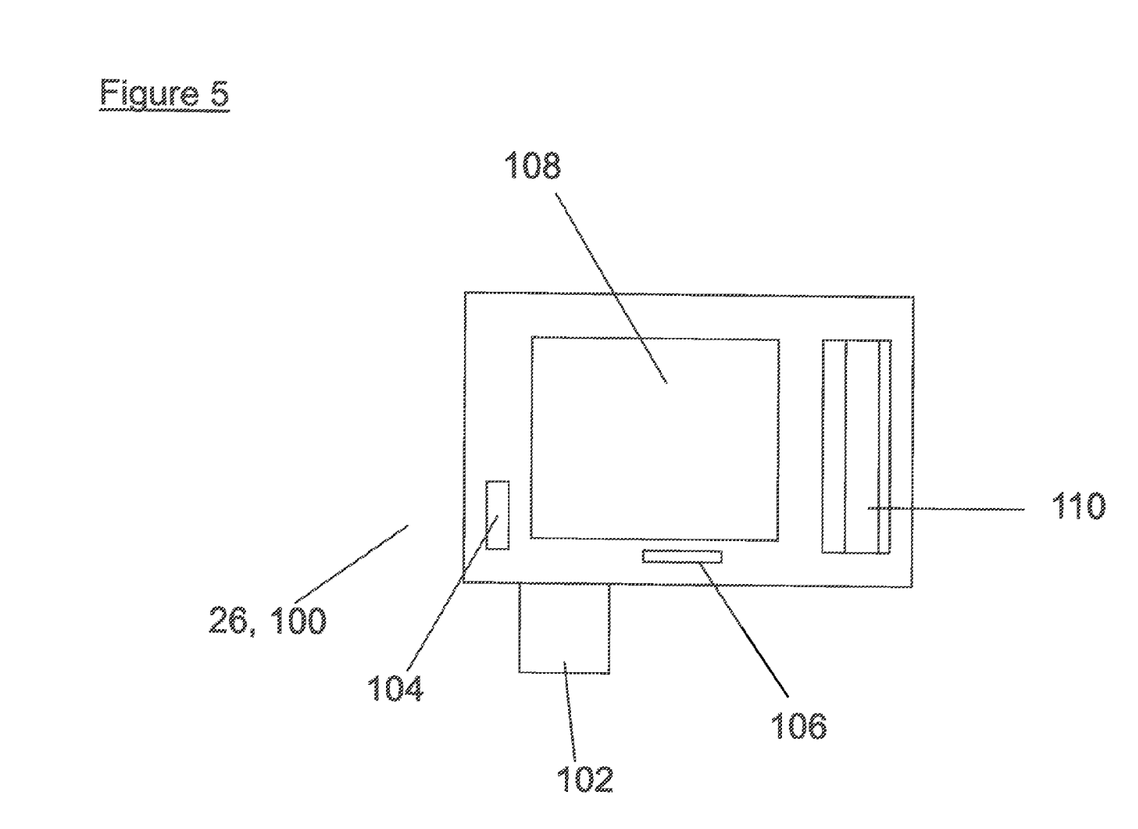
FIG. 5 comprises a pressure transducer of the invention.

At FIG. 5, there is shown a pressure transducer 26 for attachment to the catheter 2. The pressure transducer 26, which here is a preferred manifestation of a digital manometer 100, comprises an input 102, and an optional calibration interface 104. A processor 106 interprets the information gained from the transducer 26 and displays it on visual display 108, which displays real-time fluctuations in the pressure of the pleural cavity and therefore also in the second tube 22, as fluid is aspirated from it via first tube 4. The visual display can comprise any appropriate means of displaying changes in pressure, including characters such as numbers and including a gauge fluctuating around zero. A speaker 110 is provided and is connected to a tone generator (not shown). The speaker 110 is configured to provide tonal alerts as the negative pressure in the pleural cavity approaches a dangerous level, such as −20 cm H2O, The tonal alert can intensify, either in volume or in regularity or both, as the dangerous level is approached, thereby alerting the practitioner to take action.

The invention claimed is:

1. A double-skinned pleural manometry catheter comprising:
   a first catheter tube and a second catheter tube sealed from the first catheter tube,
   the first catheter tube having a first end, a second end and a bore extending therebetween to define a first tube interior, said first end adapted for insertion into a pleural cavity of a patient, the first catheter tube having a first aperture formed near the first end of the first catheter tube so as to communicate the interior of the first catheter tube with a pleural fluid within the pleural cavity of a patient, said second end of the first catheter tube remote from the first end and in communication with the first aperture by a first pleural fluid flow path, the second end of the first catheter tube configured to be external to the pleural cavity of the patient when in use, means connected to the second end of the first catheter tube for draining pleural fluid from the pleural cavity of the patient through said first pleural fluid flow path;
   the second catheter tube having a first end, a second end and a bore extending therebetween to define a second tube interior, said first end of said second catheter tube adapted for insertion into the pleural cavity of the patient, the second catheter tube having a second aperture formed near the first end of the second catheter tube so as to communicate the interior of the second catheter tube with the pleural fluid with the pleural cavity of the patient, said second end of the second catheter tube remote from the first end and in communication with the second aperture by a second pleural fluid flow path, the second end of the second catheter tube configured to be external to the pleural cavity of the patient when in use, the second end of the second catheter tube for draining pleural fluid from the pleural cavity of the patient through said second pleural fluid flow path;
   wherein pleural fluid may be drained through the first and second pleural fluid flow paths in parallel simultaneously; and
   a pressure transducer connected to the second end of the second catheter tube and adapted to continuously detect real-time fluctuations in the pressure of the pleural fluid being drained from the pleural cavity of the patient through the second pleural fluid flow path, the real-time fluctuations in the fluid pressure at in the second pleural flow path corresponding to real-time fluctuations of the pressure within the pleural cavity of the patient, and
   a processor for receiving and interpreting the real-time fluctuations detected by the pressure transducer,
   wherein the processor includes an alarm to alert a user to a change in the pleural cavity pressure dose to a predetermined negative pleural cavity pressure, and
   wherein the processor emits an audible alarm signal, the alarm signal increasingly changing in volume and/or regularity and/or periodicity in proportion to the detected pressure within the pleural cavity approaching said predetermined negative cavity pressure;
   wherein the first catheter tube is of a lesser diameter than the catheter second tube and wherein the first catheter tube is an inner tube and the second catheter tube is an outer tube, the first catheter tube running along the internal bore of the second, outer catheter tube, such that there is a space between the outer diameter of the inner catheter tube and the inner diameter of the outer catheter tube, and wherein at least a part of the second pleural flow path between the second aperture of the second catheter tube and the second end of the second catheter tube comprises the space between the inner and outer catheter tubes; and
   wherein the second catheter tube has an internal bore, the internal bore of the second catheter tube at the first end of the second catheter tube comprising a tapered portion and wherein the internal bore tapers so as to form a touching fit and is joined to the first and inner catheter tube.

2. The double-skinned pleural manometry catheter according to claim 1, wherein the inner catheter tube comprises a first, substantially straight portion and a second, curved portion.

3. The double-skinned pleural manometry catheter according to claim 2, wherein the second portion of the inner catheter tube is resiliently deformable.

4. The double-skinned pleural manometry catheter according to claim 2, wherein the first aperture is one of a plurality of first apertures, the second, curved portion having an inner diameter, the first apertures of the inner catheter tube being disposed along the inner diameter of the second, curved portion.

5. The double-skinned pleural manometry catheter according to claim 1, further comprising a valve attached to the second end of the first catheter tube and being in fluid communication with the first catheter tube, and wherein the valve is biased shut.

6. The double-skinned pleural manometry catheter according to claim 5, wherein the valve can only be opened by the projection of a solid object in a direction pointed toward the first aperture of the first catheter tube.

7. The double-skinned pleural manometry catheter according to claim 6, wherein the solid object is a needle of an integrated syringe or a non-integrated syringe.

8. The double-skinned pleural manometry catheter according to claim 1, wherein the second catheter tube comprises first and second portions, wherein the second portion is substantially perpendicularly disposed to the first portion.

9. The double-skinned pleural manometry catheter according to claim 1, wherein the first aperture is one of a plurality of first apertures, the first apertures of the inner catheter tube being oval in shape.

10. The double-skinned pleural manometry catheter according to claim 1, wherein the catheter further comprises a plate affixed to the first and second catheter tubes at a location between the first ends of the first and second catheter tubes and the second ends of the first and second catheter tubes, the plate laterally surrounding and extending radially from the first and second catheter tubes, the plate defining distal portions of the first and second catheter tubes that respectively include the first ends of the first and second catheter tubes, such that only the distal portions of the first and second catheter tubes may be inserted into the pleural cavity of the patient.

11. The double-skinned pleural manometry catheter according to claim 10 wherein the second catheter tube has a first portion including the first end of the second catheter tube and a second portion including the second end of the second catheter tube, a surface of the plate occupying a plane substantially perpendicular to the first portion of the second catheter tube.

12. The double-skinned pleural manometry catheter according to claim 1, further comprising a stabiliser for keeping the catheter firmly retained in place after insertion within said pleural cavity.

\* \* \* \* \*